United States Patent [19]

Lee et al.

[11] Patent Number: 5,840,915
[45] Date of Patent: Nov. 24, 1998

[54] PROCESS FOR THE ENATIOSELECTIVE SYNTHESIS OF INTERMEDIATES USED

[75] Inventors: Thomas Bing Kin Lee, Whitehouse Station; George Seung-Kit Wong, Summit, both of N.J.

[73] Assignee: Hoechst Marion Roussel, Inc., Cincinnati, Ohio

[21] Appl. No.: 873,631

[22] Filed: Jun. 12, 1997

Related U.S. Application Data

[60] Continuation of Ser. No. 463,144, Jun. 5, 1995, abandoned, which is a division of Ser. No. 67,892, May 27, 1993, Pat. No. 5,521,320, which is a continuation-in-part of Ser. No. 833,608, Feb. 12, 1992, Pat. No. 5,274,117, which is a continuation of Ser. No. 640,514, Jan. 3, 1991, abandoned, which is a continuation of Ser. No. 469,882, Jan. 22, 1990, abandoned.

[51] Int. Cl.$^6$ ............................................. C07D 209/34
[52] U.S. Cl. ............................................. 548/486
[58] Field of Search ............................................. 548/486

[56] References Cited

U.S. PATENT DOCUMENTS

| | | | |
|---|---|---|---|
| 3,933,840 | 1/1976 | Dahm et al. | 548/229 |
| 4,072,698 | 2/1978 | Hylton et al. | 548/498 |
| 4,329,487 | 5/1982 | Orito et al. | 560/60 |
| 4,578,509 | 3/1986 | Dolling | 562/462 |
| 4,605,761 | 8/1986 | Dolling | 562/461 |
| 4,704,472 | 11/1987 | Conn et al. | 562/461 |
| 4,704,972 | 11/1987 | Conn | 548/486 |
| 4,791,107 | 12/1988 | Hamer et al. | 514/228.2 |
| 5,093,498 | 3/1992 | Dolling | 546/134 |
| 5,274,117 | 12/1993 | Lee et al. | 548/486 |
| 5,310,935 | 5/1994 | Brossi | 548/486 |
| 5,521,320 | 5/1996 | Lee et al. | 548/486 |

FOREIGN PATENT DOCUMENTS

| | | |
|---|---|---|
| 0418770 | 3/1991 | European Pat. Off. . |
| 0438796 | 7/1991 | European Pat. Off. . |

OTHER PUBLICATIONS

Lee, Thomas et al., J. Org. Chem, vol. 56, No. 2 (1991), 872–875.
Maruzen, Institute of Japanese Chem. ed. Experimental Chemistry Lecture 18, Reaction of Prganic Compounds, II (1957( pp. 504–505) Translation provided.
Dolling, Chem. Abst., vol. 107:216813t, p. 513, No. 23, 1987.
Remy et al., Chem. Abst., 87:193907d, 1977.
Yost et al., Chem. Abst., 92:94098u, 1980.
Zoeless et al., Chem. Abst., 104:206931d, 1986.
Julian et al., J. Am. Chem. Soc., vol. 57, 1935, pp. 563–566.
Julia et al., J.C.S. Chem. Comm., vol. 17, 1978, pp. 742–743.
Dolling et al., J.Am.Chem.Soc., vol.106, 1984, pp. 446–447.
Howe et al., Chem. Abst., 83:57233w, 1975.
Kamitami et al., Chem. Abst., 85:108849c, No.15, 1976.
Schonenberger et al., J. Med.Chem., vol. 29, 1986, pp. 2268–2273.
Hughes et al., J. Org. Chem., vol. 52, 1987, pp. 4745–4752.
Chem. Abst., vol.111, No. 21, 1989.
J. of Amer. Chem. Soc., vol. 111, No. 6, 1989, pp. 2353–2355.
Chem. and Pharm. Bull., vol. 30, No.7, 1982, pp. 2641–2643.
March, Advanced Organic Chem., pp. 647–648, 1968.
Schonenberger, Heuetica Chimica Acta, vol. 69, 1986 pp. 1486–1497.
Buehler et al., "Survey of Org., Synthesis", vol.1, J. Wiley & Sons, pp. 419–421 (1977).
Buehler et al., "Survey of Org. Synthesis", vol.2, J. Wiley & Sons, pp. 400–401 (1977).
Jacques et al., "Enantiomers, Racemates, and Resolutions", 1981, J. Wiley & Sons, pp. 253–254.
Julian et al., Amer. Chem. Soc. J., vol. 56, 1934, pp. 1797–1801, entire document.
Julia, J.of Chem. Soc. Chem. Comm., Com. 532, 1978, pp. 742–743.
Mahato, Chem. Abst., vol. 107:58591n, 1987.
Chen Gang–Hua et al., "Asymmetric C–Alkylation by Chiral Phase—Transfer Catalysts" Hauxue Xuebaa, 1989, vol.47, pp. 350–354.
Lee et al., Chem. Abst., vol. 114:122098f, No. 13, 1991.
Xue–Feng Pei, Heterocycles, vol. 41, No.12, 1995.
Fundamentals of Org. Chem., J. Wiley & Sons, 1982,pp. 259–261.
Kirk–Othmer, Encyclopedia of Chem. Tech., vol. 17, pp. 325–327 (1982).
Morrison and Boyd, Organic Chemistry, 1976, Allyn and Bacon Inc., pp. 30–32, 233–235.

Primary Examiner—Ceila Chang
Attorney, Agent, or Firm—Michael J. Sayles

[57] ABSTRACT

A process for the stereoselective synthesis of [R]- and [S]-2,3-dihydro-1,3-dimethyl-2-oxo-1H-indole-3-acetonitriles comprises reacting racemic and 5-alkoxy-substituted (±)-1,3-dimethyloxindoles with a halogenated acetonitrile in the presence of a substituted N-benzyl cinchoninium, quinidinium, cinchonidinium, or quininium catalyst. The resulting alkylated oxindoles can be converted to primary amines by catalytic reduction in the presence of hydrogen gas. One of the primary amines, such as enantiomers of 3-(2-aminoethyl)-1,3-dihydro-1,3-dimethyl-5-methoxy-2H-indol-2-one, can be enriched by contact with a chiral tartaric acid in an amount sufficient to preferentially precipitate a salt of the chiral acid and one of the enantiomers. The product can be used in the synthesis of stereospecific forms of physostigmine and related compounds having pharmaceutical activity.

18 Claims, 1 Drawing Sheet

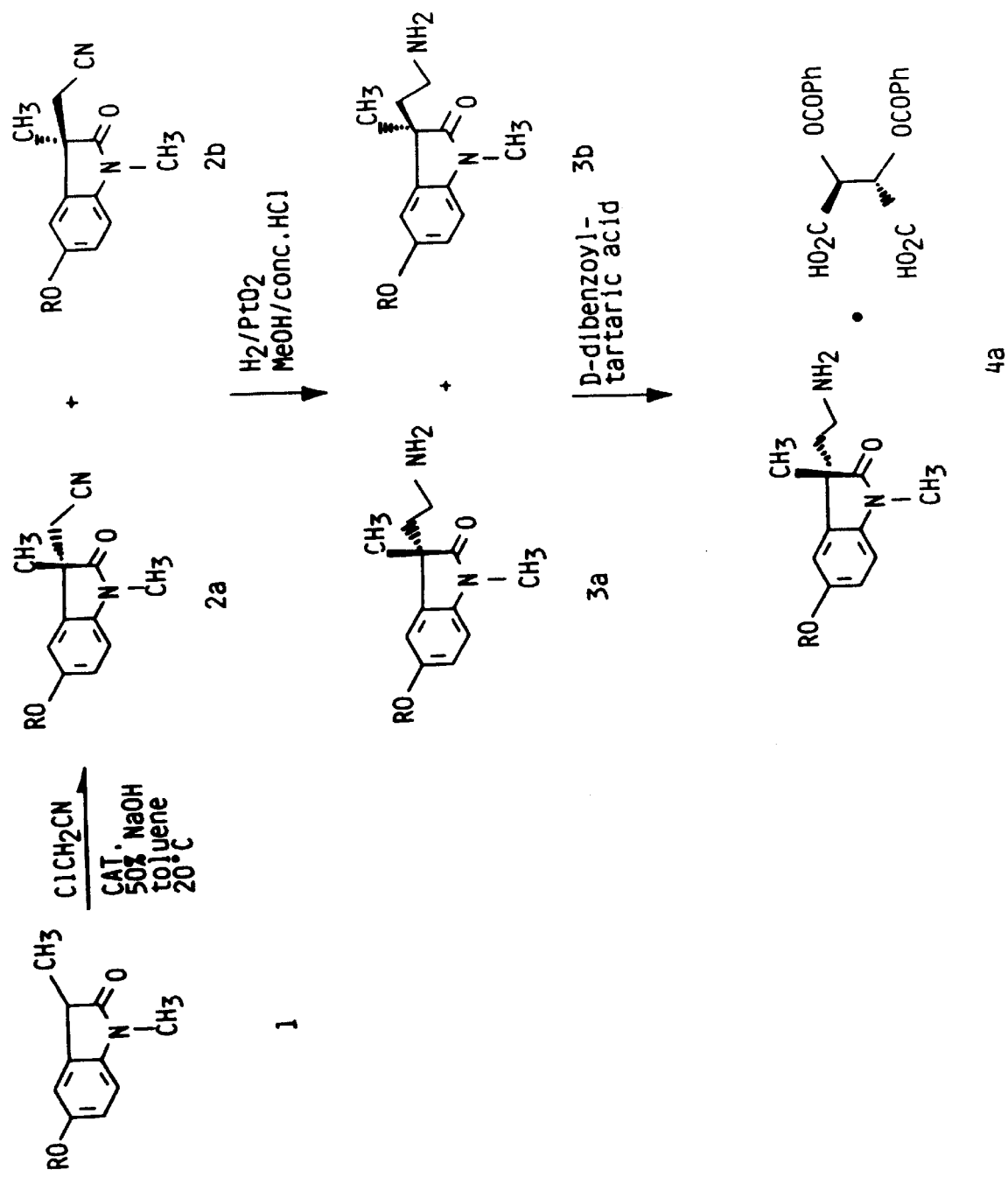

PROCESS FOR THE ENATIOSELECTIVE SYNTHESIS OF INTERMEDIATES USED

CROSS-REFERENCE TO RELATED APPLICATION

This is a continuation of application Ser. No. 08/463,144, filed Jun. 5, 1995, now abandoned which is a division of application Ser. No. 08/067,892, filed May 27, 1993, now issued U.S. Pat. No. 5,521,320; which is a CIP of application Ser. No. 07/833,608, filed Feb. 12, 1992, now issued U.S. Pat. No. 5,274,117; which is a continuation of application Ser. No. 07/640,514, filed Jan. 3, 1991, now abandoned; which is a continuation of application Ser. No. 07/469,882, filed Jan. 22, 1990, now abandoned—which is herein incorporated by reference.

BACKGROUND OF THE INVENTION

This invention relates to a process for the selective synthesis of stereoisomers. More particularly, this invention relates to a process for the stereoselective synthesis of enantiomers of nitriles and primary amines that are useful in the synthesis of (+)-physostigmine and (−)-physostigmine.

The cholinergic neuronal system can be found in the central nervous system (CNS), in the autonomic nervous system, and in the skeletal motor system. Acetylcholine (ACh) is the neurotransmitter in all ganglia, the neuromuscular junction, and the post-ganglionic synapses of the cholinergic nervous system. Acetylcholine is normally an excitatory neurotransmitter that binds to nicotinic and muscarinic receptors.

Acetylcholinesterase (AChE) is an enzyme that hydrolyzes and thereby deactivates ACh after it binds to a receptor. This enzyme is present in all peripheral and central junctional sites and in certain cells of the body.

In some circumstances, it is desirable to stimulate acetylcholine receptors. One method involves the use of indirect agonists, such as anticholinesterase drugs, which inhibit the hydrolysis of ACh by AChE. When an anticholinesterase drug blocks AChE and inhibits the destruction of released ACh, a higher neurotransmitter level and increased biological response result. The alkaloid, physostigmine, which can be isolated from the seeds of the Calabar bean, has been found to be particularly effective as an anticholinesterase drug. Physostigmine has a high affinity for AChE and is capable of inhibiting AChE for prolonged periods.

It is believed that degeneration of the cholinergic pathways in the CNS and the resultant development of apparent irregularities in neuron arrangement may be a principal cause of senile dementia of the Alzheimer type. This disease leads to progressive regression of memory and learned functions. Since the average age of the population is on the increase, the frequency of Alzheimer's disease is increasing and requires urgent attention.

It has been suggested that cholinergic agonists, such as the anticholinesterase drugs, are useful in the treatment of Alzheimer's disease. Nevertheless, drug treatment with anticholinesterase drugs has not proved entirely satisfactory. Thus, there is a need in the art for new forms of drugs for the treatment of this disease.

The enantiomers of physostigmine and pharmaceutically active physostigmine-like compounds, such as the compounds described in U.S. Pat. No. 4,791,107, are under investigation for the treatment of Alzheimer's disease. In order to satisfy the need for compounds having the highest pharmaceutical activity, there exists a need in the art for a process for the stereoselective synthesis of the enantiomers. Specifically, the enantiomer (−)physostigmine is of current interest, and while methods for preparing physostigmine and physostigmine-like compounds have been proposed, there exists a need in the art for a stereoselective process for producing the S- or (−)-forms.

It has been found that the compound 1,3-dimethyl-5-methoxyoxindolylethylamine, also referred to as 3-(2-aminoethyl)-1,3-dihydro-1,3-dimethyl-5-methoxy-2H-indol-2-one, is an important intermediate in a recently discovered method of synthesizing (−)-physostigmine. While this amine can be prepared using conventional techniques, a racemic mixture is usually formed. Resolution of the racemic amine mixture into its R and S components makes it possible to synthesize (+)-physostigmine and (−)-physostigmine.

A process for the stereoselective synthesis of the amines and their precursors could provide certain advantages. Such a process could reduce or eliminate the need for resolving mixtures of enantiomers. While stereoselective syntheses that are catalyzed by enzymes are highly enantioselective, non-enzymatic processes have a wide range of selectivity. Accordingly, the results obtained in processes based on synthetic chemical techniques are generally unpredictable, and successful results in stereoselective syntheses have been difficult to achieve.

Thus, there exists a need in the art for methods based on chemical techniques for producing enantiomers of physostigmine and physostigmine-like compounds. There also exists a need in the art for methods for the asymmetric synthesis of intermediates for use in the process. The method should make it possible to obtain the intermediates in a state of high optical purity. In addition, the process should be easy to carry out and should employ reagents that are readily available.

SUMMARY OF THE INVENTION

Accordingly, this invention aids in fulfilling these needs in the art by providing a process for the stereoselective synthesis of an oxindole, wherein the process comprises reacting a racemic oxindole of the formula

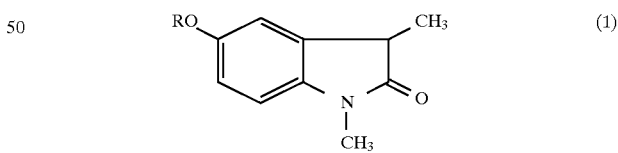

where R is selected from the group consisting of methyl, ethyl, and benzyl, with at least one equivalent of a halogenated acetonitrile selected from the group consisting of chloroacetonitrile, bromoacetonitrile, and iodoacetonitrile. The reaction is carried out in a biphasic reaction mixture having an aqueous phase comprising a strong inorganic base as a deprotonation agent, and a solvent phase comprising an organic solvent for the oxindole. The biphasic reaction mixture includes a catalytic amount of a substituted N-benzyl cinchoninium or quinidinium compound of the formula

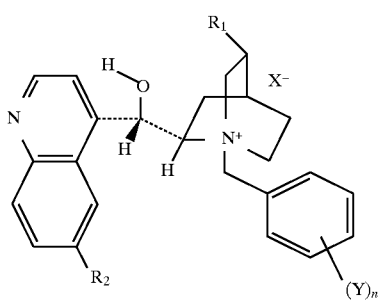

or a substituted N-benzyl cinchonidinium or quininium compound of the formula

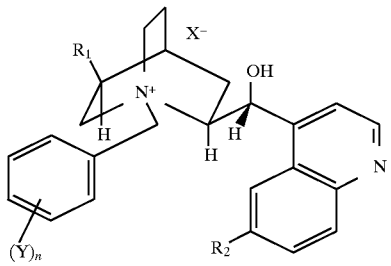

where $R_1$ is a vinyl group or an ethyl group, $R_2$ is hydrogen or a methoxy group, X is chlorine or bromine, Y is independently selected from the group consisting of hydrogen, chlorine, bromine, fluorine, trifluoromethyl groups, and nitrile groups; and n is 1, 2, 3, 4, and 5.

The 5-alkoxy-2,3-dihydro-1,3-dimethyl-2-oxo-1H-indole-3-acetonitriles that are formed in the process of this invention can be further reduced to their corresponding amines which can be used in the synthesis of stereospecific forms of physostigmine and physostigmine-like compounds. In particular, the S-form of 1,3-dimethyl-5-methoxyoxindolyl-ethylamine is useful for preparing (−)-physostigmine.

BRIEF DESCRIPTION OF THE DRAWING

This invention will be more fully understood by reference to the drawing, which depicts a reaction scheme for the asymmetric synthesis of alkylated oxindoles 2a and 2b and conversion of these compounds to primary amines 3a and 3b. The primary amines are useful in the preparation of enantiomers of physostigmine and physostigmine-like compounds having pharmaceutical activity.

DETAILED DESCRIPTION OF PREFERRED EMBODIMENTS

The asymmetric synthesis of the present invention involves conversion of an achiral substrate to a chiral product using a chiral reagent. A prochiral function serves as the precursor for a chiral product during the reaction. The following nomenclature and conventions are employed in describing this invention.

As used herein, the expression "asymmetric synthesis" means a synthesis in which an asymmetric atom, instead of being in a molecule before the commencement of the synthesis, is introduced into the molecule in the course of chemical reaction. Thus, for example, the asymmetric synthesis of the present invention is a reaction in which an achiral unit in a substrate molecule is converted by a chiral reagent into a chiral unit in such a manner that the stereoisomeric products are produced in unequal amounts.

The expression "enantioselective synthesis" means a synthesis that produces one enantiomer of a given structure in considerable predominance over the other possible enantiomer. The enantioselective synthesis of the present invention typically produces the predominant enantiomer in an amount of about 70% to about 90%, usually about 85% to about 88%, of the total enantiomers formed as products of the synthesis.

As used herein, the expressions "enantiomeric mixture" and "mixture of enantiomers" are used interchangeably to refer to racemic modifications of the enantiomers. The expressions also include solutions containing both of the enantiomers, wherein the solutions exhibit either (+) or (−) optical rotation as observed and measured with a polarimeter.

The terms "resolve" and "resolution" as used herein are intended to encompass the complete or partial separation of two enantiomers of 5-alkoxy-substituted 1,3-dimethylindolylethylamines, also referred to as 5-alkoxy substituted-3-(2-aminoethyl)-1,3-dihydro-1,3-dimethyl-2H-indol-2-one. The separation is described in more detail hereinafter. These two terms are intended to cover separations in which only one of the enantiomers is obtained in a pure state. The terms are also intended to encompass some degree of separation of the enantiomers, wherein neither of the enantiomers is obtained completely free of the other. Separation of the enantiomers may or may not be quantitative.

The heavy line in the form of a wedge ▶ in the formulas herein signifies that the substituents are above the average plane of the ring system in connection with which the wedge appears. The heavy broken lines in the form of a wedge ⋯ signify that the substituents are below the average plane of the ring system. For example, in the formula for one of the primary amines produced according to this invention, the methyl group in the 3-position is above the average plane of the oxindole ring, whereas the aminoethyl group is below the average plane of the ring. Thus, the methyl group and the aminoethyl group are trans to each other relative to the average plane of the ring.

The stereoselective synthesis of the invention can be carried out as shown in the Figure. Referring to the Figure, an oxindole 1 can be alkylated with a halogenated acetonitrile in the presence of a chiral catalyst to give an enantiomeric mixture comprising alkylated oxindoles 2a and 2b, which are terms [R]- and [S]-5-alkoxy-2,3-dihydro-1,3-dimethyl-2-oxo-1H-indole-3-acetonitrile. It was surprisingly discovered that one of the alkylated oxindoles predominates in the reaction product. In addition, it was unexpectedly found that the alkylated oxindoles 2a and 2b are obtained in relatively high chemical yield.

The crude enantiomeric mixture comprising the alkylated oxindoles 2a and 2b can be hydrogenated in the presence of a catalyst to form a mixture comprising primary amines 3a and 3b, which are terms [R]- and [S]-5-alkoxy-3-(2-aminoethyl)-1,3-dihydro-1,3-dimethyl-2H-indol-2-ones. The primary amine 3a in which R is a methyl group is an important intermediate in the preparation of (−)-physostigmine.

The primary amine should be available in as pure a form of the optical isomer as possible in order to obtain high yields and optical purity of physostigmine and physostigmine-like compounds. This can be achieved by selectively precipitating the enantiomer 3a or 3b with a chiral tartaric acid to form a tartaric acid salt 4a or 4b. One method of preparing the enantiomeric mixture 3a and 3b will now be described in greater detail.

The asymmetric synthesis of the present invention is carried out by the stereoselective alkylation of an oxindole of the formula:

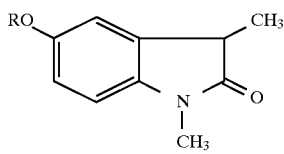

wherein the substituent R is selected from the group consisting of methyl (compound (1a)), ethyl (compound (1b)), and benzyl (compound (1c)). The oxindole 1 is a racemic mixture. The oxindole 1 is employed in the process of this invention as a racemic mixture, which can be prepared by the synthetic methods disclosed in Julian et al., *J. Chem. Soc.*, 57:563–566 and 755–757 (1935) and in U.S. Pat. No. 4,791,107.

The oxindole 1 can be selectively converted to an enantiomeric mixture comprising alkylated oxindoles 2a and 2b using a chiral phase transfer catalyst. Examples of suitable catalysts are those derived from substituted N-benzyl cinchoninium or quinidinium or N-benzyl chinconidinium or quininium halides. The reaction is characterized by high enantioselectivity.

More particularly, the stereoselective conversion of oxindole 1 to an enantiomeric mixture comprising the alkylated oxindoles 2a and 2b can be carried out by stirring a racemic mixture of the oxindole 1 and a chiral catalyst in a two-phase system comprised of a strong inorganic base and an organic solvent under an inert gas atmosphere until the reaction goes to substantial completion. Chemical conversion can be monitored by analyzing the reaction mixture by GLC for the formation of the alkylated oxindoles 2a and 2b. The enantiomer 2a or 2b that predominates is dependent upon the nature of the chiral catalyst that is employed.

The chiral catalyst for the selective conversion of oxindole 1 to the alkylated oxindole 2a or 2b is a substituted N-benzyl cinchoninium or quinidinium compound of the formula

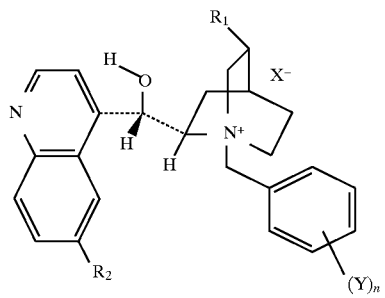

or a substituted N-benzyl cinchonidinium or quininium compound of the formula

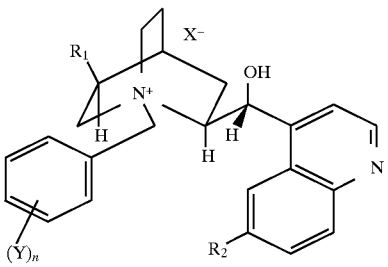

where
- $R_1$ is a vinyl group of an ethyl group,
- $R_2$ is hydrogen or a methoxy group,
- X is chlorine or bromine,
- Y is independently selected from hydrogen, chlorine, bromine, fluorine, trifluoromethyl groups, and nitrile groups; and
- n is 1, 2, 3, 4 or 5.

The substituted N-benzyl cinchoninium and the substituted N-benzyl quinidinium compounds have the formula (I) in which $R_2$ is hydrogen or methoxy, respectively. The substituted N-benzyl cinchonidinium and the substituted N-benzyl quininium compounds have the formula (II) in which $R_2$ is hydrogen or methoxy, respectively. The preferred catalysts are compounds in which Y is 3,4-dichloro or 4-trifluoromethyl. These catalysts can be prepared by utilising the procedures described in J. Ong. Chem. 1987, 52, 4745–4752 and are commercially available from Fluka Chemical Co., Hanppauge, N.Y. 11788, or from Chemical Dynamics Corporation of South Plainfield, N.J.

The substituted N-benzyl cinchoninium and quinidinium compounds and the substituted N-benzyl cinchonidinium and quininium compounds are employed in the asymmetric synthesis of the invention in an amount sufficient to catalyze the reaction of the oxindole and the halogenated acetonitrile to produce one of the enantiomers of the alkylated oxindoles in a predominant amount over the other enantiomer. For example, the catalyst can be employed in an amount of about 5 to about 50 mole % based upon the amount of oxindole 1. In a preferred embodiment of this invention, the compounds are employed as catalysts in an amount of about 10 to about 15 mole % based upon oxindole 1.

The substituted N-benzyl cinchoninium and quinidinium compounds provide the alkylated oxindole 2a in excess while the substituted N-benzyl cinchonidinium and quininium compounds yield the alkylated oxindole 2b in excess when the compounds are used in a catalytically effective amount. It will be understood that the asymmetric synthesis of this invention can also be carried out in the presence of a surfactant, such as Triton X-400. See U.S. Pat. Nos. 4,578,509 and 4,605,761.

Alkylation of the oxindole appears to proceed by conventional mechanisms. For this reason it was anticipated that a racemic mixture of the alkylated oxindoles would be obtained. Quite unexpectedly, however, it was found that the alkylation reaction was stereoselective and that either one of the enantiomers of the alkylated oxindoles can be obtained in excess, depending upon the choice of catalyst. Moreover, the predominant enantiomer is obtained in high chemical yield. The chemical yield is at least about 60% based on oxindole 1, and is generally about 65% to about 85% based on oxindole 1.

The stereoselective synthesis of this invention is carried out in a biphasic reaction mixture comprised of an organic solvent phase containing the racemic mixture of oxindole 1 and the catalyst and an aqueous phase containing a strong inorganic base. The oxindole 1 and the catalyst are dissolved in an aromatic hydrocarbon solvent. Halogenated aromatic solvents and halogenated aliphatic solvents can also be employed. Typical of the solvents that can be utilized are benzene, toluene, xylene, chlorobenzene, and methylene chloride. Solvent mixtures of hexane and cyclohexane can also be utilized. Technical grade solvents have been found to yield acceptable results. The preferred solvent is toluene because reaction mixtures containing this solvent gave the highest selectively of the alkylated oxindole 2a or 2b in the examples hereinafter. The selectivity obtained with other solvents can be optimized with a minimum of experimentation.

The aqueous phase of the reaction mixture contains a strong inorganic base, such as potassium hydroxide, sodium hydroxide, or lithium hydroxide. Technical grade bases have been found to produce acceptable results. The preferred base is sodium hydroxide because of its low cost, availability, and effectiveness in the process of the invention.

The inorganic base is employed in an amount sufficient to support catalysis of the reaction. The base functions as a deprotonation agent. It has been found that the concentration of the base in the aqueous phase affects the selectivity. The concentration of base in the aqueous phase is typically about 25% to about 50% by weight. As the concentration of base decreases, the selectivity for one of the alkylated oxindole decreases.

The aqueous phase containing the inorganic base should have minimum solubility in the organic solvent phase containing the racemic oxindole 1 and the catalyst in order to maintain a biphasic reaction mixture. The volume ratio of the organic phase of the reaction mixture to the aqueous phase is typically about 3:1 to about 10:1. A reaction mixture containing the organic phase and the aqueous phase in a volume ratio of about 5:1 has been found to produce favorable results.

The organic solvent phase and the oxindole 1 in the reaction mixture is generally about 20:1 to about 80:1, preferably about 30:1 to about 45:1. The particularly preferred ratio is about 40:1. These ratios are expressed as the volume of the organic solvent phase to the weight of the oxindole 1.

The alkylating agent for the racemic mixture of oxindole 1 can be a halogenated acetonitrile selected from the group consisting of chloroacetonitrile, bromoacetonitrile, and iodoacetonitrile. Chloroacetonitrile is the preferred alkylating agent because it has provided the highest selectivity of the alkylated oxindoles 2a and 2b. Technical grade alkylating agents have yielded satisfactory results.

The halogenated acetonitrile is employed in an amount of at least about one equivalent, and preferably about 1.1 to about 1.5 equivalents, of the racemic mixture of oxindole 1. Increasing the amount of the alkylating agent relative to the oxindole generally increases chemical yield, although there is no apparent advantage in utilizing the alkylating agent in large excess.

The stereoselective synthesis of the invention is generally carried out at a temperature of about 5° C. to about 30° C. Lower temperatures are generally accompanied by higher selectivity of the alkylated oxindole 2a or 2b, although caution must be exercised to avoid the inorganic base from separating from the aqueous solution at low temperatures. The preferred temperature range for carrying out the synthesis is about 15° C. to about 25° C., especially about 20° C.

The stereoselective synthesis of the alkylated oxindole 2a or 2b is an exothermic reaction. The reaction mixture can be cooled by internal or external means to maintain the reaction temperature. The need for cooling can be minimized and even avoided by gradually adding the halogenated acetonitrile to the biphasic reaction mixture.

It is desirable to provide an inert gas blanket over the biphasic reaction mixture in which the asymmetric synthesis is carried out in order to exclude oxygen from the reaction. Examples of suitable inert gases include nitrogen, argon, and helium. Nitrogen is preferred for economic reasons.

The stereoselective synthesis of the invention can be carried out at atmospheric pressure. Sub-atmospheric pressures should be avoided.

It has been found that alkylation of the racemic mixture of oxindole 1 proceeds very rapidly. With gradual addition of the alkylating agent to the biphasic reaction mixture, the reaction is generally complete within about 1 to about 2 hours. Shorter reaction times can be employed, although cooling of the reaction mixture may be required. Similarly, longer reaction periods can be utilized, although there is no apparent advantage in extending the reaction time. In any event, the alkylating reaction is carried to substantial completion, which can be monitored by gas chromatography or other suitable means. In order to optimize selectivity for the alkylated oxindole 2a or 2b, the reaction mixture should be agitated.

The biphasic reaction mixture can be prepared as follows. The racemic mixture of oxindole 1 can be dissolved in the organic solvent and the catalyst can be added to the resulting solution. The aqueous solution of the inorganic base can then be added to the organic solution and stirred for a sufficient period to form the biphasic reaction mixture. Mild stirring for about 10 minutes has been found to be sufficient to form the biphasic mixture. The halogenated acetonitrile employed as the alkylating agent can then be added to the biphasic reaction mixture. Slow addition of the alkylating agent improves selectivity for the predominating alkylated oxindole 2a or 2b.

The optical purity of the enantiomers formed in the process of this invention can be expressed as the excess of the enantiomer in the reaction produce as a percentage of the total enantiomers in the original solution. The amount of an enantiomer is conveniently expressed as the percent enantiomeric excess, which is abbreviated "% ee". The percent enantiomeric excess can be calculated as follows:

$$\% \, ee = \frac{([A] - [B])}{([A] + [B])} \times 100$$

where [A] is the concentration of one of the enantiomers, and

[B] is the concentration of the other enantiomer. In a completely resolved material, the enantiomeric excess is equal in weight to the total material so that % ee, and thus optical purity, is 100%. The concentration of each of the enantiomers is, of course, expressed on the same basis, and can be expressed on either a weight of molar basis because the enantiomers have the same molecular weight.

A number of substituted N-benzyl cinchoninium salts have been screened for selective conversion of oxindole 1 to alkylated oxindole 2a. All the reactions were carried out by stirring a mixture of oxindole 1 (2.5 mmol) and the appropriate catalyst (0.25 mmol) in a two-phase system consisting of 8 ml of 50% NaOH and 20 ml of toluene under nitrogen for 10 min. A solution of chloroacetonitrile (2.75 mmol) in 20 ml of toluene was then added via a syringe pump over a period of 1 hour. After completion addition, the reaction mixture was analyzed by GLC for chemical conversion. Enantiomeric excess of alkylated oxindole 2a was determined by HPLC on a Chiralcel OD column or a Chiracel OJ column (Daicel Chemical Industries Ltd.) and by NMR spectroscopy using tris[3-(heptafluoropropyl-hydroxymethylene)-d-camphorato]europium (III) as the chiral shift reagent. The results are summarized in Table I.

TABLE I

Asymmetric Alkylation of Oxindole 1
Using Chiral Phase Transfer Catalysts.

Catalysts

| Expts. | $R_1$ | $R_2$ | Y | X | % ee 2a |
|---|---|---|---|---|---|
| 1 | vinyl | H | H | Cl | >3 |
| 2 | vinyl | H | H | Br | 10 |
| 3 | vinyl | H | 2-F | Br | 5 |
| 4 | vinyl | H | 2-$CF_3$ | Br | 4 |
| 5 | vinyl | H | 2,6-$Cl_2$ | Br | >3 |
| 6 | vinyl | H | 3-F | Br | 8 |
| 7 | vinyl | H | 3-Br | Br | 48 |
| 8 | vinyl | H | 4-Br | Br | 68 |
| 9 | vinyl | H | 4-$CF_3$* | Br | 72 |
| 10 | vinyl | H | 4-CN | Br | >2 |
| 11 | vinyl | H | 3,4-$Cl_2$ | Cl | 78 |
| 12 | vinyl | H | 3,4-$Cl_2$ | Br | 77 |
| 13** | vinyl | H | 3,4-$Cl_2$*** | Cl | 17 |
| 14**** | vinyl | H | 4-$CF_3$ | Br | 61 |
| 15 | Et | H | 4-$CF_3$ | Br | 69 |
| 16 | vinyl | $OCH_3$ | H | Br | 39 |
| 17 | vinyl | $OCH_3$ | 3,4-$Cl_2$ | Br | 77 |

*4-$CF_3$BCMB
**1:1 toluene/hexanes
***3,4-$Cl_2$-BCMC
****25% NaOH

Substitution in the 3 and/or 4 position of the benzyl moiety of the catalyst with electron withdrawing groups, such as Br, Cl, or $CF_3$, significantly increased the %ee of alkylated oxindole 2a, (Expts. 7, 8, 9, and 12). This is probably due to a tighter ion-pair being formed as a result of increased positive character on the N-atom of the cinchoninium catalyst. That the observed enhancement of % ee by electron withdrawing groups is mainly due to inductive effect and not resonance effect is suggested by the low % ee observed for the 4-cyanobenzylcinchoninium bromide, (Expt. 10). The fluoro-substituted catalysts gave unexpectedly low % ee for reasons not yet identified, (Experiments 3 and 6). As expected, the dihydrocinchoninium catalyst behaved similarly to the corresponding cinchoninium salt, (Experiments 9 and 15). Unexpectedly, a moderate % ee was observed with benzylquinidinium bromide, (Experiment 16). No further improvement in % ee was observed when the benzyl group was further substituted with an electron withdrawing group, (Experiment 17). A slight counterion effect was observed for the case where the % ee of the reaction was low, (Experiments 1 and 2). When the % ee of the reaction was appreciably high, counterion effect was nonexistent.

It is generally not possible to separate predominant alkylated oxindole from the other oxindole formed in the stereoselective synthesis of the invention. Therefore, the crude mixture containing the alkylated oxindole is employed in the next step of the reaction, which involves the conversion of the nitrile groups of the alkylated oxindoles to the corresponding primary amines via catalytic reduction in the presence of hydrogen gas. This step of the reaction can be carried out using conventional techniques. For example, the crude reaction product from the stereoselective synthesis can be taken up in a suitable solvent, such as methanol, ethanol, or 2-propanol. The resulting solution can be hydrogenated in the presence of a catalytic amount of metallic catalyst, such as $PtO_2$ or platinum on carbon, in an aqueous, alcoholic, concentrated HCl medium or in acetic acid as solvent to form a mixture comprising primary amines 3a and 3b. The catalyst is typically employed in an amount of about 5% to about 50% by weight. The reaction carried out at a temperature of about 15° C. to about 30° C. for about 1 hour to about 2 hours until the reaction proceeds to substantial completion. Acids, such as sulfuric acid, phosphoric acid, and hydrobromic acid, can be employed in place of HCl. The % ee of the primary amines are formed in approximately the same relative proportion as that of the oxindoles at the start of the catalytic reduction of the nitrile.

The % ee of the primary amines 3a and 3b in the enantiomeric mixture from the reduction reaction can be further improved by resolution with an optically active derivative of tartaric acid. Different solubility characteristics of the diastereomeric salts make it possible to preferentially isolate one of the salts. More particularly, a reaction mixture containing both of the enantiomers of the primary amine in solution is allowed to interact with an optically active derivative of tartaric acid to form a salt, which readily forms a precipitate in the reaction mixture. The enantiomer in an optically purified state can be recovered from the precipitate by treatment with a mineral base.

More particularly, the enantiomers of the primary amines can be resolved with a chiral acid selected from the group consisting of dibenzoyl-D-tartaric acid, dibenzoyl-L-tartaric acid, ditoluoyl D-tartaric acid, or ditoluoyl-L-tartaric acid. The preferred chiral acid is dibenzoyl-D-tartaric acid, because the S-enantiomer of 1,3-dimethyl-5-methoxyoxindolylethylamine can be selectively precipitated from an enantiomeric mixture with this acid in relatively high optical purity. It is preferred that the chiral acid be in a substantially optically pure state. The D-form of the chiral acid can be employed to preferentially precipitate enantiomer 3a, while the L-form of the chiral acid can be employed to preferentially precipitate the enantiomer 3b.

The amount of the chiral acid employed in the enrichment process will generally be about 0.5 to about 1 equivalent of acid per equivalent of the primary amine, and preferably about 0.6 to about 0.9 equivalent. It has been found that the amount of the chiral acid used as the resolving agent can affect the identity of the enantiomer of the primary amine that is preferentially precipitated. For example, when the racemic amine 3a and 3b is treated with one or more equivalents of dibenzoyl-D-tartaric acid in an appropriate solvent, such as acetonitrile, the diastereomeric salt corresponding to the R-enantiomer 3b is preferentially precipitated. On the other hand, when less than 1 equivalent of dibenzoyl-D-tartaric acid is employed, the diastereomeric salt corresponding to the S-enantiomer 3a is preferentially precipitated. In the preferred method of carrying out the enrichment process of the invention, the enantiomer 3a is preferentially precipitated from a racemic mixture of 3a and 3b with dibenzoyl-D-tartaric acid in an amount of about 0.6 to about 0.9 equivalent of the acid per equivalent of the primary amine.

The enrichment process is carried out in a solution comprising the enantiomers and the chiral acid. The solution is prepared with an organic solvent in which the enantiomers and the chiral acid are soluble, but in which one of the tartaric acid salts of the enantiomers is less soluble so that one of the salts of the enantiomers will preferentially precipitate. The solvent is typically a liquid organic compound, such as cyclic or acyclic substituted hydrocarbon. Ethers, such as diethyl ether, dioxane, and tetrahydrofuran, can be employed. Examples of suitable halogenated solvents are methylene chloride and chloroform. The organic compound can be an aromatic compound, such as toluene of xylene. Aliphatic nitriles, such as acetonitrile and propionitrile, can also be employed. The preferred solvent is acetonitrile.

The ratio of the solvent volume to the amount of enantiomers in the mixture being resolved can be varied over a relatively broad range. The ratio of the amount of solvent to the amount of enantiomers can typically be about 5:1 to about 15:1, where the ratio is expressed as the volume of solvent relative to the weight of the enantiomers in the solvent. Preferably the ratio is about 8:1 to about 12:1. In a preferred process of carrying out this invention, the ratio of the volume of solvent to the weight of enantiomers is about 10:1.

The solution containing the enantiomers can be prepared by dissolving the enantiomeric mixture in the solvent. Dissolution can typically be carried out at a temperature of about 0° C. to about 60° C., but will generally be carried out at room temperature of about 18° C. to about 22° C. Similarly, the chiral acid can be dissolved in a solvent, which is generally the same solvent as the solvent employed for the enantiomeric mixture.

After the resolving agent is added to the solution of the enantiomers, the resulting solution is aged under conditions to form a precipitate comprising a salt of the chiral acid and the enantiomer that is selectively precipitated. Aging is typically carried out at a temperature of about 0° C. to about 30° C. The use of temperatures within the lower end of this range will generally facilitate the formation of precipitates and increase the yield because the salts are generally less soluble in the solvent at the lower temperatures. On the other hand, the use of temperatures within the upper end of this range will generally provide higher selectivity; that is, formation of one of the salts of the enantiomers will be favored over the other salt.

Resolution of the enantiomeric mixture of the primary amines according to this invention provides a precipitate of one of the enantiomers in the form of a salt of tartaric acid. The tartaric acid salt can be converted to the corresponding free base by conventional techniques. For example, the tartaric acid salt can be dissolved in water, and the resulting solution can be treated with an aqueous solution comprised of a non-toxic inorganic base in an amount sufficient to provide a substantially basic mixture. Examples of suitable bases include sodium hydroxide, potassium hydroxide, sodium carbonate, and potassium carbonate. The amine is extracted with an organic solvent from the aqueous solution. An organic solvent, such as methylene chloride, ethyl acetate, diethyl ether, or toluene, can be employed for this purpose. The organic phase can be separated from the aqueous phase. Evaporation of the solvent from the organic phase provides the amine in the form of a free base, which can generally be utilized without further purification. Conversion of the tartaric acid salt to the corresponding free base can be carried out at ambient temperatures.

The optical purity of the primary amine 3a or 3b expressed as % ee obtained by the asymmetric synthesis of this invention and resolution with the optically active derivative of tartaric acid will typically be at least about 70% ee. An optical purity of about 70% ee to about 80% ee can be attained without further purification by recrystallization. The level of optical purity can be increased to about 96–99% ee by one or two recrystallization steps. Optimum enrichment levels can be achieved with a minimum of experimentation.

The stereoselective synthesis of the alkylated oxindoles 2a and 2b according to the present invention makes it possible to substantially increase the chemical yield of the enantiomer of the primary amine 3a or 3b of interest in the enrichment step. Specifically, enrichment of an enantiomeric mixture of the alkylated oxindoles in which one of the alkylated oxindoles predominates (as in the process of the invention) will result in a higher chemical yield of the primary amine of interest than enrichment of a racemic mixture of the alkylated oxindoles, because of the higher concentration of the desired enantiomer in the starting mixture.

The concentrations of enantiomers in a reaction mixture obtained in this invention can be determined by (1) treating the primary amine with (−)-menthyl chloroformate, followed by HPLC analysis of the corresponding diastereomeric carbamates; or (2) by treating the amine with (+)-camphorsulfonyl chloride, followed by HPLC analysis of the corresponding sulfonamide. The relative composition of a mixture of enantiomers is given by the areas under the peaks corresponding to the diastereomers in HPLC chromatograms.

The absolute configuration of the enantiomer is assigned by converting the amines to known compounds whose absolute configurations have been established. For example, the absolute configuration of the carbon atom at the 10-position of the primary amine can be determined by converting the tartaric acid salts of amines 3a or 3b into the corresponding optically pure primary amine 3a or 3b by neutralization with dilute NaOH. The resulting optically pure primary amine can be reductively cyclized in high yield by refluxing the amine in n-butanol in the presence of excess sodium metal. The product can then be derivatized with (S)-(−)-α-methylbenzylisocyanate. The optical purity and absolute configuration of the resulting product can be confirmed by HPLC analysis according to the method of Schonenberger and Brossi, Helv. Chim. Acta., 69:1486 (1986).

In an alternative embodiment, the crude enantiomeric mixture comprising the alkylated oxindoles 2a and 2b is subjected to a preferential recrystallization whereby a desired, optically pure, e.g. R-enantiomer or S-enantiomer, alkylated oxindole in high optical purity is separated from the residual remaining racemate. The racemate is preferentially precipitated leaving the optically pure oxindole in the filtrate.

A suitable recrystallization solvent is selected. Such solvent is selected from (1) a suitable protic solvent, such as an alcohol, e.g. methanol, ethanol, isopropanol, etc., (2) a suitable aprotic solvent, such as an aliphatic ether, e.g., tertiary-butyl methyl ether, isopropylethyl ether, etc. and (3) a suitable mixture of a protic and aprotic solvent.

The enantiomeric mixture comprising the alkylated oxindoles 2a and 2b is treated with the recrystallization solvent at a suitable temperature, typically at room temperature or slightly higher, e.g. 25°–30° C., for a sufficient period of time to effect complete dissolution of the mixture. The resultant solution, comprising the dissolved mixture of 2a and 2b and selected recrystallization solvent, is then allowed to cool to room temperature and/or allowed to remain at room temperature for a short period of time, e.g. typically 5 to 10 minutes, whereupon a major amount, typically 65 to 82%, of a first, pure enantiomer (either R or S) which is originally present in the mixture of 2a and 2b in an enriched amount thereof, will remain in solution; and whereupon a residue comprising a mixture of the other, second enantiomer and the remainder of the first enantiomer will precipitate out of solution as a solid mixture.

The resulting two phase mixture of pure enantiomer in solution and precipitated solid is optionally, but preferably, cooled to a temperature of about 0° C. to about 5° C., e.g. by means of an ice bath, for a period of time to insure complete precipitation out of the resultant residue solid mixture of enantiomers.

As previously indicated, alkylation of the oxindole proceeds via a stereoselective process and either one of the enantiomers of the alkylated oxindoles is obtained in excess, depending upon the choice of catalyst employed. Accordingly, either the R-enantiomer or the S-enantiomer can be present in the enantiomeric mixture of 2a and 2b in an enriched amount. It is this enriched enantiomer which is separated from the precipitated solid mixture comprising at least the other enantiomer.

The resulting two-phase mixture is then subject to a conventional separation, e.g. filtration, whereby the precipitated residue is separated from the filtrate containing the first, optically pure enantiomer. The filtrate is then concentrated using conventional means, e.g. rotoevaporation, and the first, optically pure enantiomer is separated, e.g. by filtration. The resulting first enantiomer is of high optical purity.

The first enantiomer can then be treated further to form the amine, 3a or 3b, and thereafter to form eserethole or esermethole, using conventional techniques well known in the art, e.g. Yu & Brossi, Heterocycles, 1988, Vol. 27, 1709, in either the R or S configuration. Employing the teachings of Lee et al., *J. Org. Chem.*, 1991, Vol. 56, 872, the eserethole can be converted to physostigmine and related compounds.

In particular, the optically pure first enantiomer is reduced with hydrogen in acetic acid in the presence of platinum oxide. Amine 3a or 3b is then treated with ethyl chloroformate in the presence of triethylamine in toluene. Reductive cyclization using lithium aluminum hydride in tetrahydrofuran followed by chromotographic purification provided pure eserethole or esermethole of high optical purity.

The resultant eserethole or esermethole is reacted with fumaric acid in a conventional manner, e.g. typically at 45° to 50° C. for 0.5 to 1 hours to form a fumarate salt which is recrystallized from methanol to give essentially 100% enantiomeric purity.

This invention will be more fully understood by reference to the following examples in which all parts, proportions, ratios, and percentages are by weight unless otherwise indicated.

Chiral Phase Transfer Alkylation

Example 1

N-[4-(Trifluoromethyl)benzyl]cinchoninium bromide

To a solution containing 0.48 g of (±)-5-methoxy-1,3 dimethyloxindole in 20 ml of toluene was added, under nitrogen, 0.13 g (10 mole %) of N-[4-(trifluoromethyl) benzyl]cinchoninium bromide (4-CF$_3$-BCNB) followed by 8 ml of 50% NaOH. After stirring the mixture for 10 minutes, a solution containing 0.21 g of chloroacetonitrile in 20 ml of toluene was added dropwise over 1 hour. After complete reaction, 25 ml of ice-cold water was added. The mixture was filtered through a small celite pad rinsing with 10 ml of coluene. The filtrate was transferred to a separatory funnel, and the 2 layers were separated. The toluene extract was concentrated under reduced pressure and the residue was analyzed on a Daicel Chiralcel OD column eluting with a 10% isopropanol-hexane mixture. The enantiomeric excess of compound 2a in which R is methyl was determined to be 72%.

Example 2

N-[3,4-(Dichloro)benzyl]cinchoninium Chloride As Catalyst

The procedure described in Example 1 was repeated with 0.12 of N-[3,4-(dichloro-benzyl]cinchoninium chloride (3,4-Cl$_2$-BCNC) in identical fashion. The enantiomeric excess of compound 2a in which R is methyl was found to be 78% as determined by HPLC assay of the reaction mixture.

Example 3

N-[4-Bromobenzyl]cinchoninium Bromide As Catalyst

The procedure described in Example 1 was repeated with 0.14 g of N-[4-bromobenzyl]cinchoninium bromide (4-Br-BCNB) in identical fashion. The enantiomeric excess of compound 2a in which R is methyl was found to be 68% as determined by HPLC assay of the reaction mixture.

Example 4

N-[3-Bromobenzyl]cinchoninium Bromide As Catalyst

The procedure described in Example 1 was repeated with 0.14 g of N-[3-bromobenzyl]cinchoninium bromide (3-Br-BCNB) in identical fashion. The enantiomeric excess of compound 2a in which R is methyl was found to be 48% as determined by HPLC assay of the reaction mixture.

Example 5

N-Benzylquinidinium Bromide As Catalyst

The procedure described in Example 1 was repeated with 0.13 g N-benzylquinidinium bromide (BQNC) in identical fashion. The enantiomeric excess of compounds 2a in which R is methyl was determined to be 39% by HPLC assay of the reaction mixture.

Example 6

N-[3,4-Dichlorobenzyl]quinidinium Chloride As Catalyst

The procedure described in Example 1 was repeated with 0.20 g of N-[3,4-dichlorobenzyl]quinidinium chloride (3,4-Cl$_2$-BQNC) in identical fashion. The enantiomeric excess of compound 2a in which R is methyl was determined to be 77% by HPLC assay of the reaction mixture.

Example 7

N-[4-Trifluoromethyl)benzyl]dihydrocinchoninium Bromide As Catalyst

The procedure described in Example 1 was repeated with 0.13 g of N-[4-(trifluoromethyl)benzyl]

dihydrocinchoninium bromide (4-CF$_3$-H$_2$-BCNB) in identical fashion. The enantiomeric excess of compound 2a in which R is methyl was found to be 69% by HPLC assay.

Example 8

N-[4-Chlorobenzyl]cinchoninium Bromide As Catalyst

The procedure described in Example 1 was repeated with 0.13 g of N-[4-chlorobenzyl]cinchoninium bromide (4-Cl-BCNB) in identical fashion. The enantiomeric excess of compound 2a in which R is methyl was found to be 70% by HPLC assay of the reaction mixture.

Example 9

N-[3,4-(Dichloro)benzyl]cinchoninium Bromide As Catalyst

The procedure described in Example 1 was repeated with 0.12 g of 3,4-Cl$_2$-BCNB in identical fashion. The enantiomeric excess of compound 2a in which R is methyl was found to be 77% as determined by HLPC assay of the reaction mixture.

Example 10

Step (A): N-[3,4-(Dichloro)benzyl]cinchonium Chloride As Catalyst

To a mixture containing 5.0 g of (±)-5-methoxy-1,3 dimethyloxindole and 1.92 g of 3,4-Cl$_2$-BCNC (15 mole %) in 200 ml of toluene was added under an efficient N$_2$ purge 40 ml of 50% NaOH. After stirring this mixture for 10 min., a solution containing 2.17 g of choloracetonitrile in 20 ml of toluene was added over 1 hour. After complete reaction, the mixture was cooled to 10°–15° C., and 160 ml of ice-cold H$_2$O was added. The reaction mixture was filtered through a Celite pad rinsing with 40 ml of toluene. The combined filtrate was transferred to a separatory funnel, and the 2 layers were separated. The toluene solution was extracted with 100 ml of cold 3N HCl, and 100 ml of cold H$_2$O. After evaporation of solvent, 5.02 g (83%) of compound 2a in which R is methyl was isolated as a slightly brownish oil. The entntiomeric excess of compound 2a was determined to be 73% by HPLC.

Step (B): Catalytic Reduction of Nitriles to Primary Amines

The nitrile, 2a, obtained from Step (A) was taken up in 50 ml of methanol and 7.25 ml of concentrated hydrochloric acid. A sample of 0.5 g of PtO$_2$ was added. The mixture was subjected to hydrogenation for 3 hours at 45 psi. The catalyst was removed by filtration through filter paper rinsing with 15 ml of methanol. The combined filtrate was concentrated under reduced pressure, and the residue was dissolved in 100 ml of ice-cold water. The acidic aqueous solution was first extracted with 50 ml of methylene chloride, and then basified with 5 ml of 50% NaOH. The basic aqueous chloride solution was extracted with methylene chloride (3×50 ml). The combined organic extract was dried (Na$_2$SO$_4$) and concentrated under reduced pressure giving 4.70 g (92%) of the corresponding amine, 3a.

Step (C): Enrichment of Amine by Selective Precipitation With Chiral Tartaric Acid The amine, 3a, from Step (B) was dissolved in 25 ml of acetonitrile. A solution containing 6.42 g of dibenzoyl-D-tartaric acid in 25 ml of acetonitrile was added rapidly under nitrogen. After stirring for another 30 minutes, the precipitate that formed was filtered to give 10.38 g of a white solid. The solid was recrystallized from 60 ml of 10% water-acetonitrile mixture giving 7.86 g (47.4%) of the tartrate salt of the amine; m.p. 136°–137° C. The optical purity was determined to be 99% by means of derivatization with (+)-camphorsulfonyl chloride followed by HPLC analysis of corresponding sulfonamide.

Example 11

N-[4-(Trifluoromethyl)benzyl]cinchonidinium Bromide As Catalyst

Use of this catalyst gives predominantly the isomer leading to (+)-physostigmine.

To a stirred solution containing 1.19 g of 1,3-dimethyl-5-methoxyoxindole and 0.83 g of chloroacetonitrile in 50 ml of toluene and 10 ml of 50% NaOH under nitrogen was added 0.53 g of the above catalyst in 1 portion. After 30 min, the layers were separated. The toluene solution was washed with water, and then concentrated under reduced pressure to give the desired product in quantitative yield. The enantiomeric excess (ee) of enantiomer 2b was determined to be 41% in the following manner. The nitrile was reduced to the corresponding amine as described in Step (B) of Example 10, followed by derivatization of the amine with (−)-menthylchloroformate with HPLC analysis of the resultant carbamate on a Whatmann Partisil PXS 10/25 column eluting with 10% acetonitrile/methylene chloride (2 ml/min; 254 mm detection).

Example 12

N-[3-(Trifluoromethyl)benzyl]cinchoninium Bromide As Catalyst

The procedure described in Example 1 was repeated with 0.13 g of N-[3-(trifluoromethyl)benzyl]cinchoninium bromide (3-CF$_3$-BCNB) in identical fashion. The enantiomeric excess of compound 2a was found to be 68% as determined by HPLC assay of the reaction mixture.

Example 13

N-[3,4-(Dichloro)benzyl]cinchoninium Chloride as Catalyst and (+)-5-Ethoxy-1,3-dimethyloxindole as Substrate To a mixture containing 2.15 g of (±)-5-ethoxy-1,3-dimethyloxindole, also referred to as 1,3-dihydro-1,3-dimethyl-5-ethoxy-2H-indol-2-one and 0.77 g of 3,4-Cl$_2$-BCNB (15 mole %) in 80 ml of toluene was added under an efficient N$_2$ purge 16 ml of 50% NaOH. After stirring this mixture for 10 min., a solution containing 0.87 g of chloroacetonitrile in 8 ml of toluene was added over 1 hour. After complete reaction, 48 ml of ice cold H$_2$O was added. The reaction mixture was filtered through a Celite pad rinsing with 20 ml of toluene. The combined filtrate was transferred to a separatory funnel, and the two layers were separated. The toluene solution was extracted with 20 ml of 2N HCl, and twice with 20 ml of H$_2$O. After evaporation of solvent, the slightly brownish oil was assayed on a Daicel Chiralcel OD column eluting with a 10% isopropanol-hexanes mixture. The enantiomeric excess of the compound 2a in which R is ethyl was determined to be 71%.

Example 14

N-[3,4-(Dichloro)benzyl]cinchoninium Chloride as Catalyst and (+)-5-Benzyloxy-1,3-dimethyloxindole as Substrate The procedure described in Example 13 was repeated with 2.80 g of (±)-5-benzyloxy-1-1,3-dimethyloxindole, also referred to as 5-benzyloxy-1,3-dihydro-1,3-dimethyl-2H-indol-2-one in identical fashion. The enantiomeric excess of compound 2a in which R is benzyloxy was determined to be 73% by means of HPLC assay on a Daicel Chiralcel OJ column eluting with 40% isopropanol-hexanes.

The compound (±)-5-methoxy-1,3-dimethyl-oxindole employed in the Examples is also referred to as 1,3-dihydro-1,3-dimethyl-5-methoxy-2H-indol-2-one.

Example 15

A. (3S)-1,3-Dimethyl-5-Ethoxyoxindolyl-3-Acetonitrile

To a 2 L 3-necked RB-flask fitted with a mechanical stirrer, $N_2$-inlet, thermometer, condenser, and a rubber septum (threaded with a polyethylene rubing connected to a 50 mL syringe) was added 50 g of 1,3-dimethyl-5-ethoxyoxindole, 2.49 g of [N-(3,4-dichlorobenzyl) cinchoninium chloride (2 mole %) and 625 mL of toluene. This was followed by the addition of 125 mL of 50% NaOH solution. The biphasic mixture was stirred for 15 minutes. To this mixture was then added a solution containing 20.33 g of chloroacetonitrile (1.1 equivalents) in 31 mL of toluene via a syringe pump. After complete reaction, the biphasic mixture was cooled to about 10° C., and 500 mL of ice cold $H_2O$ was slowly added. The reaction mixture was filtered through Celite. The reaction flask and the Celite pad was rinsed with 300 mL of toluene. The 2 phases were separated. The aqueous phase was extracted once with 300 mL toluene. The combined toluene solutions were extracted twice with 150 mL portions of 3N HCl, once with $H_2O$ (300 mL) and once with a saturated NaCl solution (300 mL). The toluene solution was concentrated under reduced pressure to give 68.0 g (>100%) of 1,3-dimethyl-5-ethoxyoxindolyl-3-acetonitrile (S/R 87/13 by chiral hplc) as a solid. The above solid residue was dissolved in 177 mL of hot methanol. The clear solution was cooled to room temperature and then at 0°–5° C. for 30–40 minutes. The precipitated solid was filtered and washed with 20 ml of cold methanol, air dried to give 14.08 g (23.7%) of essentially pure racemic 1,3-dimethyl-5-ethoxyoxindolyl-3-acetonitrile as a solid. The filtrate was concentrated to give 44.45 g (74.7%) of highly pure (3S)-1,3-dimethyl-5-ethoxyoxindolyl-3-acetonitrile (S/R 99/1 by chiral hplc).

Examples 16–22

The procedure of Example 15 was repeated except that various 5-substituted 1,3-dimethyl oxindoles were employed with various recrystallization solvents. The results of these syntheses are given in the TABLE below.

TABLE

Recrystallization of 1,3-Dimethyl-5-alkoxyoxindolyl-3-acetonitrile

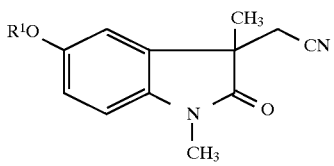

| Example | $R^1$ | Solvent | Dilution[a] (v/w) | Before[b] % ee(R or S) | After[c] % ee(R or S) |
|---|---|---|---|---|---|
| 16 | Methoxy | iPr$_2$O | 29 | 70(S) | 78(S) |
| 17 | Methoxy | $^t$BuOCH$_3$ | 7 | 70(S) | 75(S) |
| 18 | Methoxy | 95 EtOH | 5 | 70(S) | 82(S) |
| 19 | Methoxy | MeOH | 3 | 70(S) | 82(S) |
| 20 | Ethoxy | $^t$BuOCH$_3$ | 23 | 73(S) | 91(S) |

TABLE-continued

Recrystallization of 1,3-Dimethyl-5-alkoxyoxindolyl-3-acetonitrile

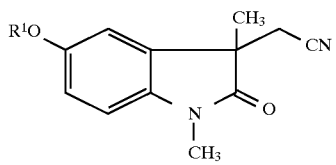

| Example | $R^1$ | Solvent | Dilution[a] (v/w) | Before[b] % ee(R or S) | After[c] % ee(R or S) |
|---|---|---|---|---|---|
| 21 | Ethoxy | MeOH | 9 | 73(S) | 83(S) |
| 22 | Ethoxy | MeOH | 4 | 74(S) | 98(S) |
| 23 | Ethoxy | MeOH | 9 | 52(R) | 95(R) |

[a]based on the theoretical amount of pure enantiomer available
[b]% ee of the crude oxindole
[c]% ee of the filtrate

Example 24

R-Eserethole Fumarate

A. R-Eserethole

To a solution containing 49.1 g of (3R)-1,3-dimethyl-5-ethoxyoxindolyl-3-acetonitrile (95% ee) in 246 mL of acetic acid is added 2.46 (g) of platinum oxide. The mixture is hydrogenated for 7 h at 45 psi at room temperature. The reaction mixture is filtered and the filtrate is concentrated under reduced pressure. The residue is partitioned between toluene and a dilute sodium hydroxide solution. The toluene solution is concentrated to give 51.92 g of the corresponding amine.

To a solution of 49.9 g of the above amine and 24.29 g of triethylamine in 500 mL of toluene at 0° C. is added, under nitrogen, 23.87 g of ethyl chloroformate. After complete addition, the mixture is allowed to warm up to room temperature and stirred for 4 h. The reaction mixture is washed with water and the toluene solution is dried over anhydrous sodium sulfate. The filtrate is concentrated under reduced pressure to give 60.21 g of the corresponding carbamate.

To a solution of 42.07 g of the carbamate in 106 mL of tetrahydrofuran at 0° C., is added under nitrogen, 273 mL of a 1M solution of lithium aluminum hydride in tetrahydrofuran. After the addition is complete, the mixture is heated under reflux for 1.5 h. After a standard workup, the residue is purified by chromatography on silica gel to give 17.58 g of (R)-eserethole (95% ee).

B. (R)-Eserethole Fumarate

To a solution containing 38 g of eserethole (R/S 97.5/2.5) in ethanol is added a hot solution of 21.49 g of fumaric acid in ethanol. The warm mixture is allowed to cool to room temperature, and then cooled further in an ice-bath. The precipitate that formed is filtered to give 47.6 g of white crystals. This is re-crystallized again from 190 mL of methanol to give 37.8 g of the fumarate as white crystals. Chiral hplc assay of this material showed that it is 100% optically pure.

The process of this invention has a number of advantages. The process for the stereoselective synthesis of enantiomers provides precursors of physostigmine and physostigmine-like compounds in high chemical yield and purity. The availability of one enantiomer of a give structure in considerable predominance over other enantiomers makes it possible to enhance the results obtained when the enantiomers are subsequentially resolved. The techniques for carrying out the stereoselective synthesis do not present any unusual difficulties. The reagents required for the process are readily available or can be easily prepared using conventional techniques. This invention provides a practical, economical process for the total synthesis of selected enantiomers of physostigmine and related compounds.

We claim:

1. A process for the synthesis of essentially enantiomerically pure 3-aminoalkyloxindole, wherein the process comprises:

(a) reacting at a temperature of about 15° C. to about 25° C. a racemic oxindole of the formula

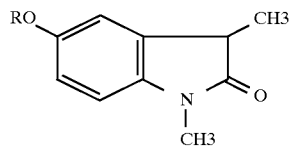

where R is methyl, with at least one equivalent of chloroacetonitrile in a biphasic reaction mixture having an aqueous phase comprising sodium hydroxide as a deprotonation agent and a solvent phase comprising toluene and a catalytic amount of a compound of the formula

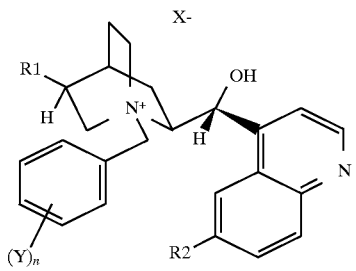

wherein n is 1 or 2;

$R_1$ is vinyl, $R_2$ is hydrogen, Y is 4-Br and X is Br; and $R_1$ is vinyl, $R_2$ is hydrogen, Y is 4-$CF_3$ and X is Br; or $R_1$ is vinyl, $R_2$ is hydrogen, Y is 3,4-dichloro and X is Cl; or $R_1$ is vinyl, $R_2$ is hydrogen, Y is 3,4-dichloro and X is Br; or $R_1$ is ethyl, $R_2$ is hydrogen, Y is 4-$CF_3$ and X is Br; or $R_1$ is vinyl, $R_2$ is $OCH_3$, Y is 3,4-dichloro and X is Br; to thereby form two enantiomers of the resulting alkylated oxindole, wherein one of said enantiomers is in an amount of about 68% to about 90% enantiomeric excess relative to the other enantiomer;

(b) treating the mixture with a recrystallization solvent selected from alcohol, aliphatic ether and mixture thereof to selectively dissolve the excess of one of said enantiomer to form a solution containing essentially one of said enantiomer and to form a precipitate containing a racemic mixture of one of said enantiomer and the other enantiomer, then, separating said solution from said precipitate and recovering from the solution the optically pure one of said enantiomer;

(c) converting nitrile groups of the resulting alkylated oxindoles to corresponding said aminoalkyloxindole by catalytic reduction in the presence of hydrogen gas to form a mixture of enantiomers of primary amines; and (d) contacting the mixture of enantiomers of the said aminoalkyloxindole with a chiral acid in an amount sufficient to preferentially precipitate a salt of the chiral acid and one of the enantiomers, and recovering the resulting precipitate, wherein the chiral acid is selected from the group consisting of dibenzoyl-D-tartaric acid and ditoluoyl-D-tartaric acid.

2. The process according to claim 1, wherein $R_1$ is vinyl, $R_2$ is hydrogen, Y is 4-Br and X is Br.

3. The process according to claim 1, wherein $R_1$ is vinyl, $R_2$ is hydrogen, Y is 4-$CF_3$ and X is Br.

4. The process according to claim 1, wherein $R_1$ is vinyl, $R_2$ is hydrogen, Y is 3,4-dichloro and X is Cl.

5. The process according to claim 1, wherein $R_1$ is vinyl, $R_2$ is hydrogen, Y is 3,4-dichloro and X is Br.

6. The process according to claim 1, wherein $R_1$ is ethyl, $R_2$ is hydrogen, Y is 4-$CF_3$ and X is Br.

7. The process according to claim 1, wherein $R_1$ is vinyl, $R_2$ is $OCH_3$, Y is 3,4-dichloro and X is Br.

8. The process according to claim 1, wherein the chiral acid is dibenzoyl-D-tartaric acid or ditoluoyl-D-tartaric acid.

9. The process according to claim 8, wherein the ratio of the volume of solvent to the total weight of enantiomers of the primary amines is about 8:1 to about 12:1.

10. The process according to claim 8, wherein the ratio of the volume of solvent to the total weight of enantiomers of the primary amines is about 10:1.

11. The process according to claim 9, wherein the solvent is acetonitrile.

12. The process according to claim 11, wherein the chiral acid is employed in an amount of about 0.5 to about 1 equivalents of acid per equivalent of enantiomers of primary amines.

13. The process according to claim 1, wherein the primary amine is obtained in an optical purity of at least about 70% ee.

14. The process according to claim 12, which further comprises basifying the resulting tartaric acid salt to form the corresponding free base.

15. The process according to claim 14, wherein the tartaric acid salt is dissolved in water and the resulting solution is neutralized with an aqueous inorganic base.

16. The process according to claim 15, which further comprises extracting amine from the aqueous solution with an organic solvent and isolating the amine by evaporation of the solvent.

17. The process according to claim 16, wherein the solvent for extraction is selected from the group consisting of methylene chloride, ethyl acetate, diethyl ether and toluene.

18. The process according to claim 17, wherein the inorganic base for neutralization is selected from the group consisting of sodium hydroxide, potassium hydroxide, sodium carbonate and potassium carbonate.

* * * * *